US005111805A

United States Patent [19]

Jaggy et al.

[11] Patent Number: 5,111,805

[45] Date of Patent: May 12, 1992

[54] PIEZOELECTRIC TRANSDUCER

[75] Inventors: Peter Jaggy, Ötisheim; Werner Krauss, Knittlingen; Dagobert Schäfer, Bretten; Helmut Wurster, Oberderdingen, all of Fed. Rep. of Germany

[73] Assignee: Richard Wolf GmbH, Knittlingen, Fed. Rep. of Germany

[21] Appl. No.: 574,331

[22] Filed: Aug. 28, 1990

[30] Foreign Application Priority Data

Oct. 3, 1989 [DE] Fed. Rep. of Germany ....... 3932959

[51] Int. Cl.[5] ...................... A61B 17/22; H01L 41/08; H04R 17/00

[52] U.S. Cl. .............................. 128/24 EL; 310/311; 310/313; 310/334; 310/335; 367/157; 367/165; 367/171; 367/173

[58] Field of Search ..................... 128/24 AA, 24 EL; 319/311, 313 A, 313 B, 313 R, 328, 331, 334, 335, 800; 367/157, 165, 166, 171, 173

[56] References Cited

U.S. PATENT DOCUMENTS 4,156,863 5/1979 Madison et al. .................... 367/165
4,431,934 2/1984 Kleinschmidt et al. ............ 310/328
4,539,554 9/1985 Jarvis et al. ......................... 310/311
4,618,796 10/1986 Riedlinger ........................... 310/311
4,651,310 3/1987 Kaneko et al. ........................ 310/325
4,704,556 11/1987 Kay ..................................... 367/165
4,721,106 1/1988 Kurtze et al. .................. 128/24 EL
4,807,627 2/1989 Eisenmenger .................. 128/24 EL
4,858,597 8/1989 Kurtze et al. .................. 128/24 EL
4,869,768 9/1989 Zola ............................. 84/DIG. 24
4,879,993 11/1989 Reichenberger et al. ..... 128/24 EL
4,972,826 11/1990 Koehler et al. ................ 128/24 EL

FOREIGN PATENT DOCUMENTS 0324948 7/1989 European Pat. Off. ....... 128/24 EL
036701 8/1989 European Pat. Off. ....... 128/24 EL

*Primary Examiner*—Kyle L. Howell
*Assistant Examiner*—Krista M. Pfaffle
*Attorney, Agent, or Firm*—Panitch Schwarze Jacobs & Nadel

[57] ABSTRACT

There is disclosed, a piezoelectric transducer for generating focussed ultrasonic shock waves for use in lithotripsy. The ultrasonic shock waves are emitted in pulsed form and can be transmitted by way of a coupling medium to the body of a patient to be treated. The transducer comprises a substantial member of individual piezoelectric transducer elements of ceramic or like material which are connected to the poles of a pulse generator and are fixed to a support in mosaic form and with their sides electrically insulated from one another. The acoustic termination of the transducer elements is essentially free from reflection. An intermediate medium of at least one layer, the acoustic impedance of which lies between that of the ceramic of the transducer element and that of the coupling medium, is provided between the transducer elements and the coupling medium. The thickness d of the layer is chosen in accordance with the relationship $d > \tau_k \cdot c_{LA}$, where $\tau_k$ is the propagation time of sound in the piezoceramic of the transducer elements and $c_{LA}$ is the sound velocity in the intermediate medium.

19 Claims, 7 Drawing Sheets

PIEZOELECTRIC TRANSDUCER

FIELD OF THE INVENTION

This invention relates to a piezoelectric transducer for producing pulsed form, focused ultrasonic shock waves for use in lithotripsy, for transmission by way of a coupling medium to the body of a patient to be treated by means of said shock waves, the transducer comprising; a piezoelectric transducer element support; a pulse generator; and a substantial number of individual piezoelectric transducer elements made of ceramic or like material, and being connected to the poles of the pulse generator and fixed to said support in mosaic form, and being laterally insulated from one another, said transducer elements being acoustically terminated in essentially reflection free fashion.

BACKGROUND OF THE INVENTION

Piezoelectric transducers are described in principle, for example in DE-B-34 25 992 (U.S. Pat. No. 4,721,106). The use of a coupling medium for coupling ultrasonic shock waves to a patient's body with such transducers is known.

Although transducers have been successfully used in therapy, the structural dimensions thereof need to be very large, if the energy density at the focus is to be sufficient for the disintegration of a concretion which is to be destroyed.

Although the energy densities that can be produced by means of piezoelectric materials are very high, only a very small proportion of the energy produced is, in practice, passed into the coupling medium, which may be water or oil, since the sound-producing ceramic and the water or oil differ very greatly from one another acoustically.

SUMMARY OF THE INVENTION

An object of the present invention is thus to provide a transducer of the type described above in which the energy density of the ultrasonic shock waves at its focus is high enough to enable the structural dimensions of the transducer to be reduced.

According to the invention there is provided between the transducer elements and the coupling medium, an intermediate medium of at least one layer, the acoustic impedance of which lies between that of the ceramic of the transducer elements and that of the coupling medium, the thickness of the layer being chosen so that the relationship $d > \tau_k \cdot c_{LA}$ applies, where $\tau_k$ is the propagation time of sound in the piezoceramic of the transducer elements and $c_{LA}$ is the sound velocity in the particular intermediate medium.

The dimensioning of the thickness of said layer of intermediate medium cannot be determined with the aid of the wavelength of the ultrasound in the present case, since the ultrasonic shock waves generated by the transducer have a very broad frequency spectrum. In this respect adjustment according to the teaching of U.S. Pat. No. 4,156,863 does not contribute to the achievement of the object set forth above. According to U.S. Pat. No. 4,156,863, it is merely envisaged that the thickness of a casting composition which has the acoustic impedance of the coupling medium (water) is chosen as one quarter of the wavelength of the sound waves emitted by the individual modulators. In the present case the conditions for impedance adjustment are quite different, since it is not the individual frequency or wavelength, but the propagation time of the sound through the individual transducer elements, that is the basis for all the considerations.

If a layer of the intermediate medium is introduced between the active surface of each piezoelectric transducer element and the coupling medium, said layer must have a certain thickness and a certain acoustic impedance if optimum results are to be achieved. Since this is not a matter of resonance matching, the damping in the intermediate layers is of no great importance so long as it does not assume extreme values, and the thickness needed, which is determined by the relationship set forth above, is not exceeded by several times.

The acoustic impedance to be chosen depends on the acoustic circumstances at the boundary between the active transducer elements and the layer of the intermediate medium, or on the known sound transmission factors at the boundary between two media of different acoustic impedance. In all cases said acoustic impedance lies between that of the ceramic of the transducer elements and that of the coupling medium.

The acoustic thickness of the layer of the intermediate medium must be greater than that of the ceramic of the transducer elements.

The energy entering the coupling medium can be increased by providing a plurality of layers of intermediate media between the transducer elements and the coupling medium, the acoustic impedances of which decrease, in the direction of radiation of the ultrasonic shock waves, from the first layer on the transducer elements.

In all cases only some of the sound will pass through each boundary layer, because a portion thereof will always be reflected. Such reflection will always be soft, that is to say phase reversal will occur, since the impedance of each intermediate medium is greater than that of the next of of the coupling medium. When the reflected portion of the sound then encounters the previous boundary layer, the reflection will be hard, that is to say without phase reversal, some of the reflected portion then running into the next layer of intermediate medium or, finally, into the coupling medium.

The layer or layers of the intermediate media may each be assigned to one transducer element, uniformly to all of the transducer elements, or partly to all the transducer elements and partly to one transducer element.

A transducer according to the invention may be self-focusing, that is to say, for example, cup-shaped or it may be planar. In the latter case, at least one layer of intermediate medium to be constructed as an acoustic lens. This layer then acts to focus the ultrasonic shock waves at the focus of the transducer, so that an additional expenditure need not be incurred.

The transducer may contain, in the direction of radiation of the ultrasonic shock waves, a first layer of intermediate medium on the transducer elements having a surface electrically connecting the transducer elements to one another and facing the transducer elements, such surface being connected to one pole of the pulse generator. Said first layer thus constitutes a common electrode for all of the transducer elements, whereby not only is the expenditure on wiring considerably reduced but the transducer is overall more compact and is less susceptible to malfunction. To this end, said first layer is preferably massive and metallic, being for example of aluminium, the acoustic impedance of which complies with the relationship set forth above. Where the transducer is planar said first layer may be constructed as a massive acoustic lens, for focusing the ultrasonic shock waves at the transducer focus.

Each transducer element may have a backing, the acoustic impedance of which is at least as high as that of the ceramic or like material of the individual transducer elements. Almost reflection-free termination to the transducer elements is thereby ensured so that negative jerking pulses which are undesirable in lithotripsy are limited to the minimum possible in practice. The backings may be so constructed so that the sound originating from the ceramic or like material is scattered on the reverse sides of the backings and is not, therefore, focused at the focus of the transducer. To this end the reverse sides of the backings may, for example, be roughened or may be of appropriate shaping, being for example, conical.

Nevertheless, all of the transducer elements may be provided with a common backing providing for their reflection-free termination.

In all of the embodiments described above, the energy density of the ultrasonic shock waves at the transducer focus is increased in comparison with that of known transducers by "passive" means, that is to say by improved linking of the ultrasonic shock waves with the coupling medium, in effect by the better use of the energy generated by the transducer elements. Some embodiments described below, however, also enable the energy density at the transducer focus to be increased by "active" means, in particular, by enabling the transducer elements to be driven by higher voltages, with safety, and without reducing the service life of the transducer.

To this end the transducer elements may be secured to the support, which is electrically conductive, by means of electrically conductive fixing means, the support being connected to the other pole of the pulse generator, whereby the transducer elements can be driven by means of higher voltages without the transducer elements ripping from their anchorage.

The embodiments described above where said first layer of intermediate medium on the transducer elements is massive and metallic and thus serves as an electrode, can be driven by higher voltages, with greater ease, whereby the emission capacity of the transducer is actively increased, if the space enclosed by said first layer, said common backing and said support are sealed off in liquid- and gas-tight fashion by means of electrical non-conductive side walls, and said space being filled with a highly insulating medium, which may be a gas, oil, or a solid insulator, for example.

The transducer may be constructed so that an electrically conductive first layer provides the support which is connected to one pole of the pulse generator, the support, and a housing, surrounding a space which is sealed off in liquid- and gas-tight fashion and is filled with a highly insulating medium. The energy density of the ultrasonic shock waves generated by the transducer at the focus is thereby increased, on the one hand by virtue of improved radiation capacity and on the other hand by virtue of improved coupling of the energy and the coupling medium.

According to another embodiment of the invention in which the increase in the energy density at the focus is ensured both actively and passively, the first layer consists of a highly insulating casting material which also fills intermediate spaces between the transducer elements. Said first layer effects not only impedance adjustment but electrically insulates the sides of the transducer elements from one another, whereby the transducer can be driven at increased voltages.

Suitable casting materials are, in particular, polyurethanes, epoxy mixtures or silicones.

BRIEF DESCRIPTION OF THE DRAWINGS

In the drawings, the same components are denoted by the same reference symbols.

DETAILED DESCRIPTION OF THE INVENTION

Figure 1:
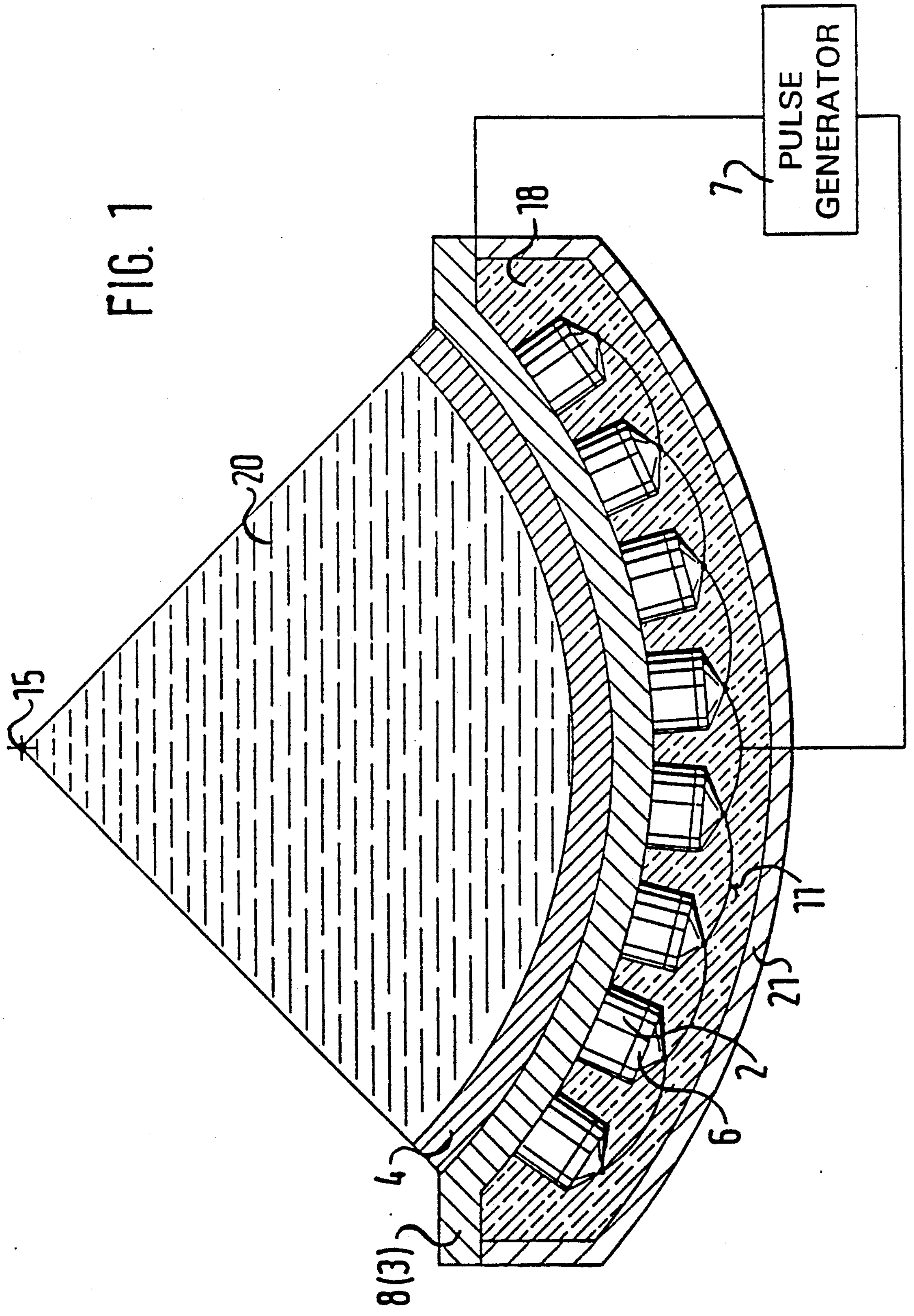
FIGS. 1 to 9, are schematic sectional views of piezoelectric transducers according to first, second, third, fourth, fifth, sixth, seventh, eighth and ninth embodiments of the invention, for producing focused ultrasonic shock waves for use in lithotripsy.

As shown in FIG. 1 a cup-shaped and, therefore, self-focusing transducer, according to the first embodiment comprises ceramic piezoelectric transducer elements 2 for focussing an ultrasonic shock wave generated by way of a coupling medium 20, for example water, at a focus 15. The active surfaces of the transducer elements 2 are fixed on a support 8. In this embodiment, the support 8 is identical with a first layer 3, the thickness D of which is chosen according to the relationship $d > \tau_k \cdot c_{LA}$, where $\tau_k$ is the propagation time of sound in the piezoceramic of the transducer elements 2 and $c_{LA}$ is the sound velocity in the layer 3.

There is applied to the layer 3 another layer 4 of an intermediate medium which serves to adjust the impedance, and the acoustic impedance of which lies between that of the layer 3 and that of the coupling medium 20. The said relationship applies to the thickness of the layer 4, $c_{LA}$ being the sound velocity in the layer 4, in this case.

In this first embodiment, the layer 3 or the support 8 is electrically conductive, being massive and metallic, and serves as a common electrode for all of the transducer elements 2, and is therefore connected to one pole of a pulse generator 7. The other pole of the generator 7 is connected by wiring 11 to the reverse ends, opposite to said active surfaces, of the transducer elements 2, by way of conical, electrically conductive individual backings 6. The conical shape of the backings 6 ensures that sound originating from said reverse ends is scattered so that it is not focused at the focus 15.

The layer 3 or the carrier 8 is preferably made of aluminium if the coupling medium 20 is water.

The construction of the first layer 3 as a massive support 8 enables the layer 3 in cooperation with a housing 21, to define a liquid- and gas-tight space filled with a highly insulating medium 18. The medium 18 prevents sparks from flashing to the individual transducer elements 2 when a high voltage is applied thereto. The transducer of FIG. 1 can accordingly be driven at a voltage allowing of a considerably higher emission capacity than in the case of known transducers.

Figure 2:
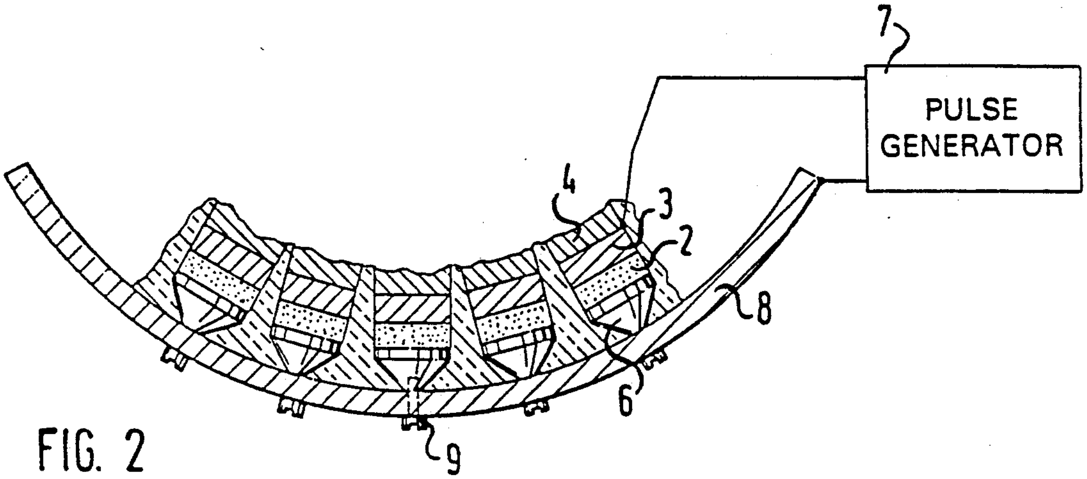

In the embodiment of FIG. 2 the reverse ends of transducer elements 2 of a cup-shaped transducer are secured to electrically conductive individual backings 6 and to an electrically conductive support 8 by means of screws 9. Two layers 3 and 4 of intermediate media are applied to the transducer elements 2 for adjusting the acoustic impedance to the coupling medium (not shown). The first layer 3 is electrically conductive, for conducting voltage from pulse generator 7 to the transducer elements 2. The other pole of the generator 7 is connected to the transducer elements 2 by way of the support 8, the screws 9 and the backings 6.

Figure 3:
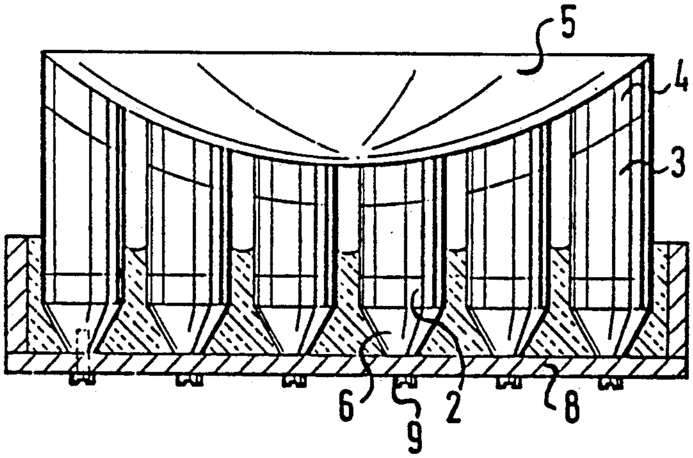

In a planar transducer according to the embodiment of FIG. 3, transducer elements 2 are secured to individual backings 6 and to support 8 by means of screws 9. Adjustment of the acoustic impedance is achieved by means of three layers 3, 4 and 5 of intermediate media, on the transducer elements 2, the conditions set out above for the acoustic impedances of these layers of course being met. The layer 5, which is assigned to all of the transducer elements 2 together, is constructed as an acoustic lens which, together with the first layer 3 effects focusing of the radiated ultrasonic shock waves.

Figure 4:
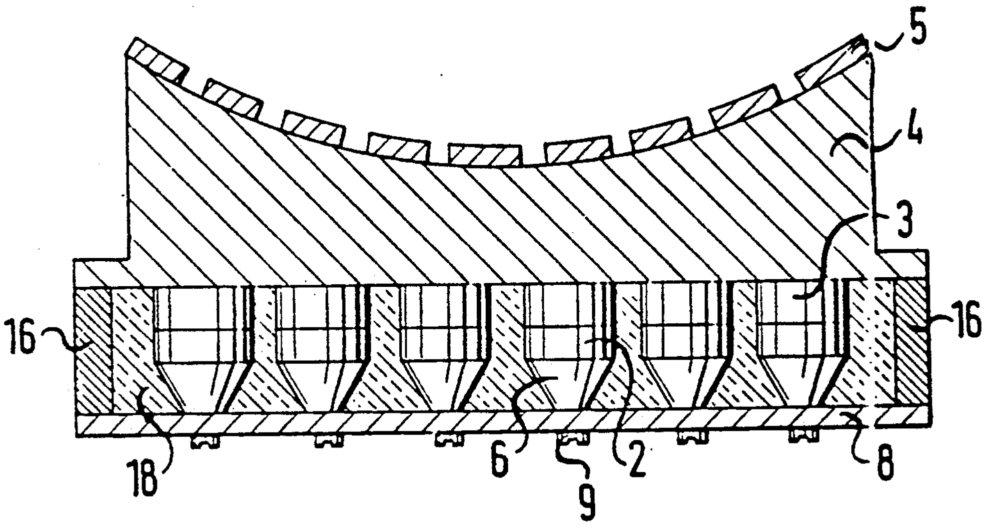

In a planar transducer according to the embodiment of FIG. 4, three layers 3, 4 and 5 of intermediate media are applied to transducer elements 2, which are secured, as explained above with reference to FIG. 3, in the direction of radiation of the ultrasonic shock waves. The middle layer 4 is provided as a common layer and is constructed as a focusing acoustic lens. Electrically nonconductive side walls 16, the common support 8 and the layer 4 enclose a liquid- and gas-tight space filled with a highly insulating medium 18.

Figure 5:
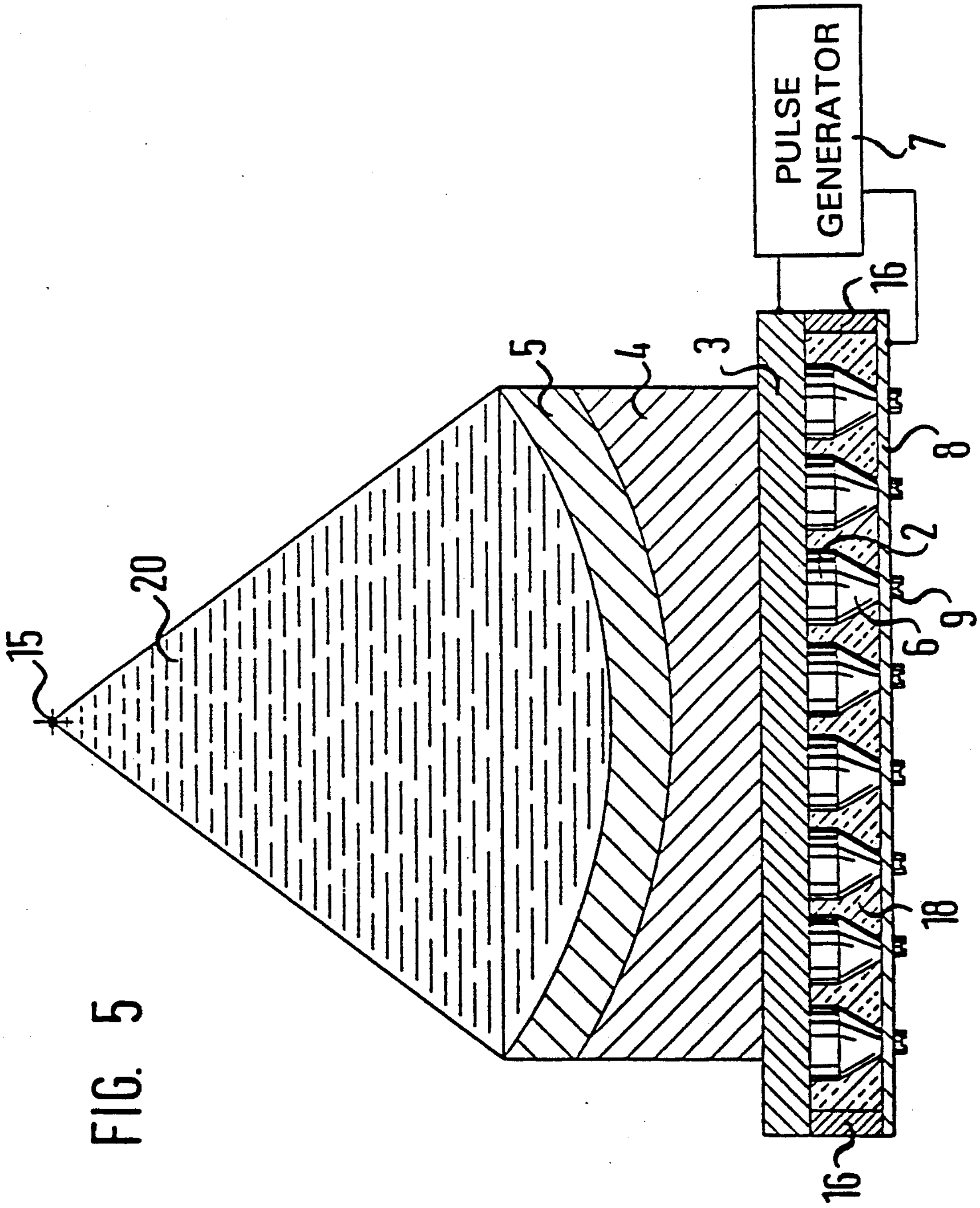

A similar embodiment to that of FIG. 4, is shown in FIG. 5. In this embodiment, however, all of layers 3, 4 and 5 are uniformly assigned to all of the transducer elements 2 together, the layers 4 and 5 having a lens function.

Figure 6:
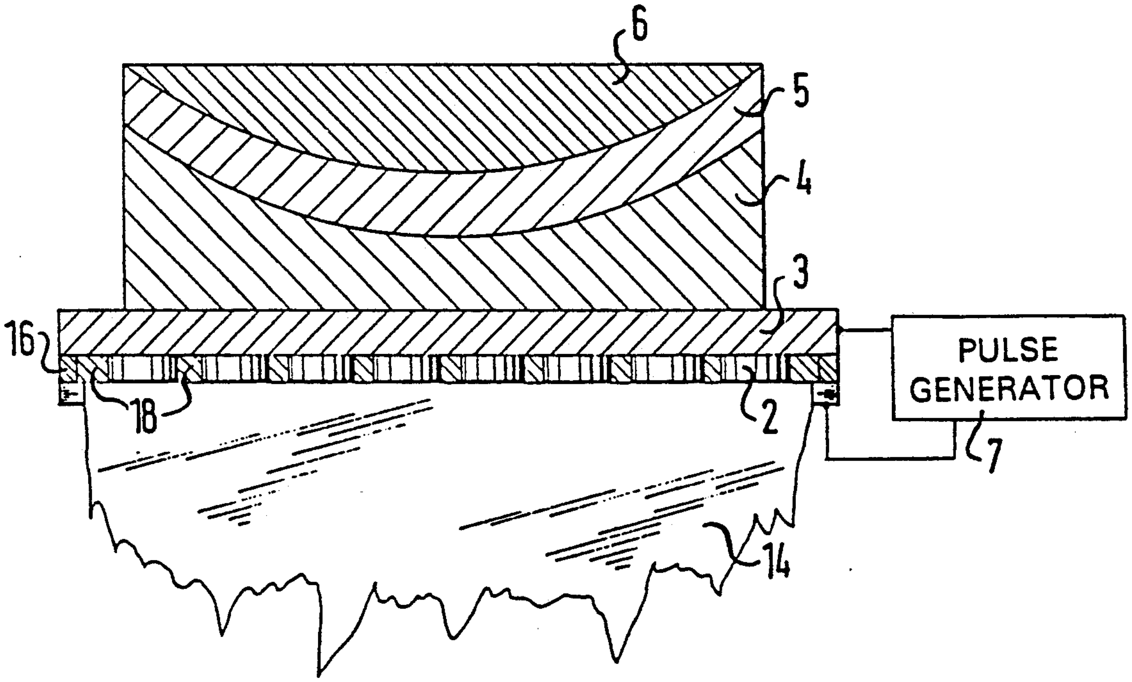

In the embodiment of FIG. 6, transducer elements 2 have a common backing 14, which also seals off the space enclosed by the first layer 3 and the electrically non-conductive side walls 16 and which contains a highly insulating medium 18. The reverse side of the backing 14 is shaped so that sound reflected therefrom is not focused at the focus of the transducer. All of layers 3 to 6 are assigned to all of the transducer elements together, layers 4 and 5 being constructed as lenses for focusing the ultrasonic shock waves.

Figure 7:
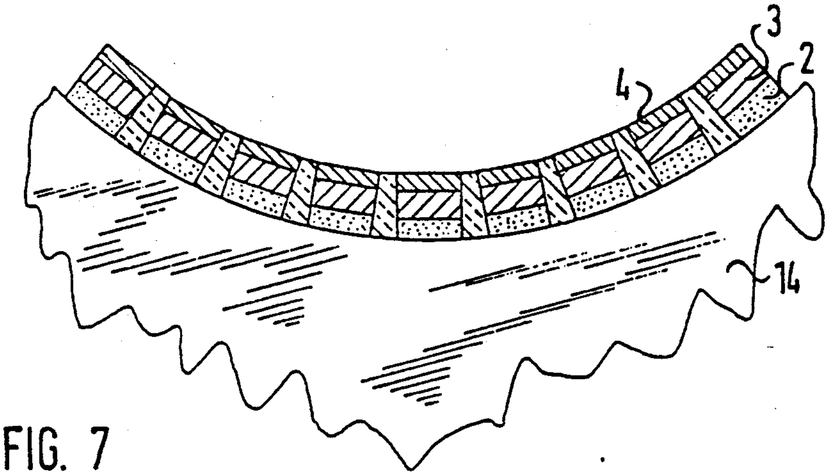

As shown in FIG. 7, a cup-shaped transducer can also have a common backing 14. The layers 3 and 4 of said intermediate media are each assigned only to one transducer element 2.

Figure 8:
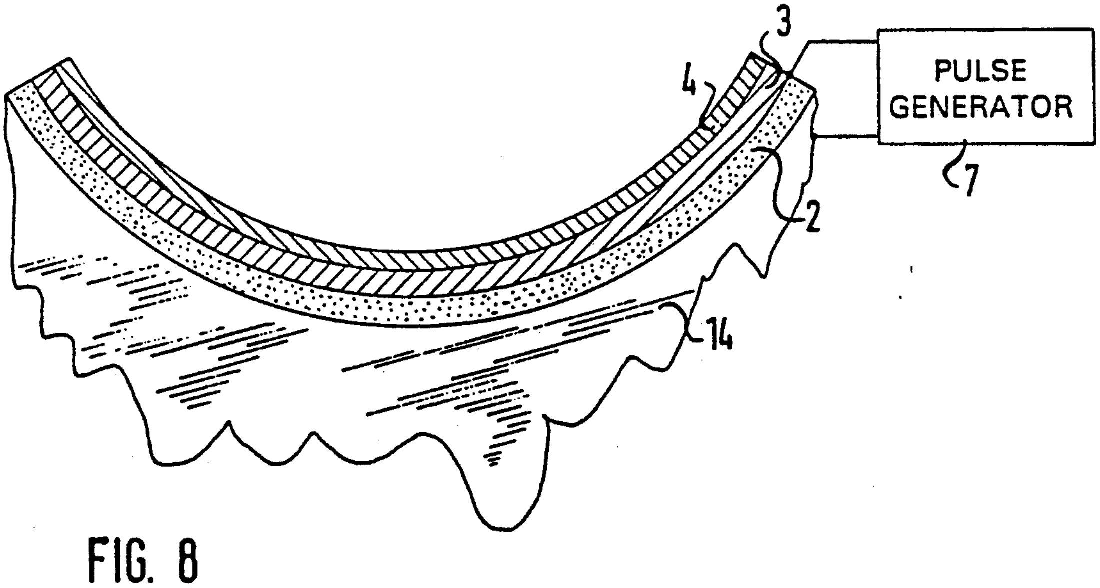

According to the embodiment of FIG. 8 which shows an extreme case where piezoceramic material 2 is provided in one piece, the material 2 is terminated on the reverse side by a backing 14. Acoustic impedance adjustment is effected by means of two layers 3 and 4 of said coupling media.

Figure 9:
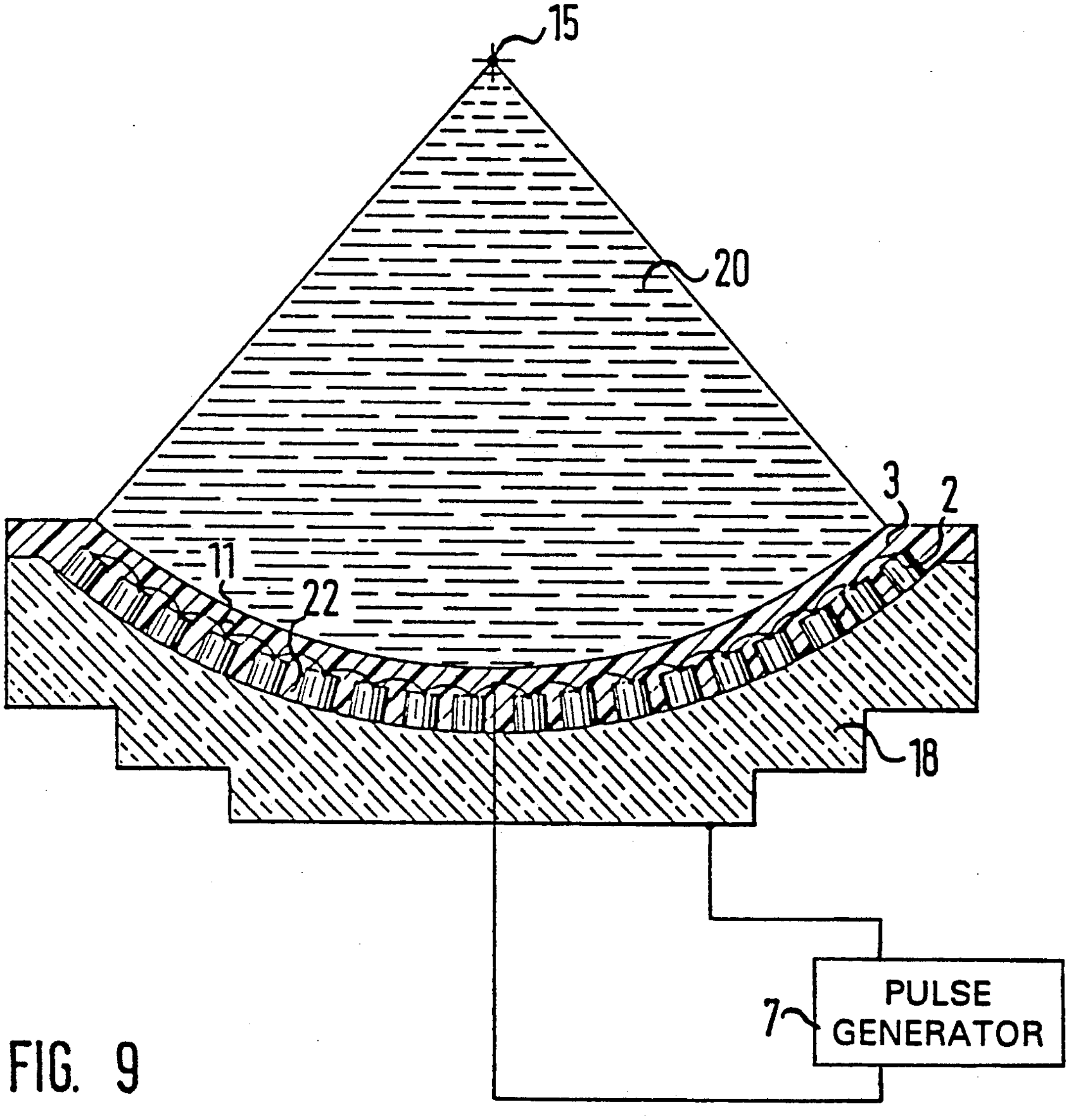

In FIG. 9, which shows a particularly preferred embodiment of the invention, only one layer 3 of an intermediate medium is shown. The layer 3 consists of a highly insulating casting material, consisting for example, of polyurethanes, epoxy mixtures or silicones. Said casting material has an acoustic impedance which again lies between that of the ceramic of transducer elements 2 and that of coupling medium 20. Intermediate spaces 22 between the individual transducer elements 2 are filled with said casting material. The transducer of this ninth embodiment can be driven at higher voltages than known transducers because of the insulation provided by said casting material. Moreover the transducer element 2 is embedded in completely waterproof fashion in casting material, so that the transducer has outstanding non-susceptibility to malfunction.

What is claimed is:

1. A piezoelectric transducer for producing pulsed, focused ultrasonic shock waves for use in lithotripsy, for and transmission by way of a coupling medium to the body of a patient to be treated by means of said shock waves, said transducer comprising:

a piezoelectric transducer element support;

a pulse generator;

a plurality of individual piezoelectric transducer elements made of a material selected from the group consisting of ceramic material and ceramic-like material, and each of said elements being connected to each of the poles of the pulse generator and fixed to said support in mosaic form, and being laterally insulated from one another, said transducer elements being acoustically terminated in essentially reflection free fashion; and at least one layer of an intermediate medium interposed between said transducer elements and said coupling medium, the acoustic impedance of which ,at least one layer lies between that of the material of said transducer elements and that of said coupling medium, the thickness of d said layer being chosen in accordance with the relationship $d > \tau_k \cdot c_{LA}$, where $\tau k$ is the propagation time of sound in said material of said transducer elements and $c_{LA}$ is the sound velocity in said intermediate medium.

2. A transducer as claimed in claim 1, wherein a plurality of layers of said intermediate medium are provided between said transducer elements and said coupling medium, the acoustic impedances of said layers decreasing from said transducer elements to said coupling medium in the direction of radiation of the ultrasonic shock waves.

3. A transducer as claimed in claim 1, comprising a plurality of layers of said intermediate medium, each layer being assigned to an individual one of said transducer elements.

4. A transducer as claimed in claim 1, comprising a single layer of said intermediate medium assigned to all of said transducer elements.

5. A transducer as claimed in claim 1, comprising a plurality of layers of said intermediate medium, each layer being assigned to all of said transducer elements.

6. A transducer as claimed in claim 1, comprising a plurality of layers of said intermediate medium, at least one layer being assigned to all of said transducer elements and at least one layer being assigned to an individual one of said transducer elements.

7. A transducer as claimed in claim 1, comprising a plurality of layers of said intermediate medium, at least one of said layers being constructed as an acoustic lens.

8. A transducer as claimed in claim 1, comprising a plurality of layers of said intermediate medium, a first of said layers in the direction of radiation of said shock waves being connected to one of the poles of said pulse generator, and the surface of said first layer which faces said transducer elements, electrically connecting said transducer elements to each other.

9. A transducer as claimed in claim 8, wherein said first layer is metallic.

10. A transducer as claimed in claim 9, wherein said first layer is constructed as an acoustic lens.

11. A transducer as claimed in claim 1, wherein each of said transducer elements has a backing, the acoustic impedance of said backing being at least as great as that of said material of said transducer elements.

12. A transducer as claimed in claim 11, wherein each backing has a reverse side constructed for scattering sound reflected therefrom.

13. A transducer as claimed in claim 1, comprising a backing common to all of said transducer elements, for said essentially reflection-free termination thereof.

14. A transducer as claimed in claim 1, comprising electrically conductive fixing means securing said transducer elements to said support, said support being connected to one of the poles of said pulse generator.

15. A transducer as claimed in claim 13, comprising a plurality of layers of said intermediate medium, wherein said support, said common backing, and one of said layers form walls enclosing a space, electrically insulating and closing-off said space in a fluid-tight fashion, and a highly insulating material filling said space.

16. A transducer as claimed in claim 1, wherein said support is provided by an electrically conductive layer of said intermediate medium, said support being connected to one of the poles of said pulse generator, and further comprising a housing cooperating with said support to enclose a space which is closed off in fluid tight fashion, and a highly insulating material filling said space.

17. A transducer as claimed in claim 1, wherein said first layer of said intermediate medium consists of a highly insulating casting material, said transducer elements defining spaces therebetween and said casting material filling said spaces.

18. A transducer as claimed in claim 17, wherein said casting material is selected from the group consisting of polyurethanes, epoxy mixtures and silicones.

19. A piezoelectric transducer for producing pulsed focused ultrasonic shock waves for use in lithotripsy, and for transmission by way of a coupling medium to the body of a patient to be treated by means of said shock waves, said transducer comprising:

a piezoelectric transducer element support;

a pulse generator;

a piece of piezoelectric transducer material selected from the group consisting of ceramic material and ceramic-like material, and being connected to each of the poles of the pulse generator and fixed to said support, said transducer element material being acoustically terminated in essentially reflection free fashion; and at least one layer of an intermediate medium interposed between said transducer element material and said coupling medium, the acoustic impedance of which at least one layer lies between that of the material of said transduces elements and that of said coupling medium, the thickness d of said layer being chosen in accordance with the relationship $d > \tau_k \cdot c_{LA}$, where $\tau_k$ is the propagation time of sound in said material of said transducer element strip and $c_{LA}$ is the sound velocity in said intermediate medium.

* * * * *